(12) United States Patent
Hayamizu et al.

(10) Patent No.: US 10,308,772 B2
(45) Date of Patent: Jun. 4, 2019

(54) METHOD FOR PRODUCING PSEUDOPOLYROTAXANE AQUEOUS DISPERSION

(71) Applicant: Sumitomo Seika Chemicals Co., Ltd., Hyogo (JP)

(72) Inventors: Naohisa Hayamizu, Hyogo (JP); Hiroki Okazaki, Hyogo (JP); Akira Kimura, Hyogo (JP); Shinya Okazaki, Hyogo (JP)

(73) Assignees: Sumitomo Seika Chemicals Co., Ltd., Hyogo (JP); Advanced Softmaterials Inc., Chiba (JP)

( * ) Notice: Subject to any disclaimer, the term of this patent is extended or adjusted under 35 U.S.C. 154(b) by 0 days.

(21) Appl. No.: 15/540,520

(22) PCT Filed: Jan. 8, 2016

(86) PCT No.: PCT/JP2016/050511
§ 371 (c)(1),
(2) Date: Jun. 28, 2017

(87) PCT Pub. No.: WO2016/111353
PCT Pub. Date: Jul. 14, 2016

(65) Prior Publication Data
US 2017/0349711 A1    Dec. 7, 2017

(30) Foreign Application Priority Data

Jan. 9, 2015 (JP) ................................. 2015-003287

(51) Int. Cl.
| C08J 3/03 | (2006.01) |
| C08J 3/00 | (2006.01) |
| C08L 71/02 | (2006.01) |
| C08L 5/16 | (2006.01) |
| C08G 83/00 | (2006.01) |
| B82Y 5/00 | (2011.01) |
| C08B 37/16 | (2006.01) |

(52) U.S. Cl.
CPC . *C08J 3/03* (2013.01); *B82Y 5/00* (2013.01); *C08B 37/0015* (2013.01); *C08G 83/007* (2013.01); *C08J 3/005* (2013.01); *C08L 5/16* (2013.01); *C08L 71/02* (2013.01); *C08G 2650/04* (2013.01)

(58) Field of Classification Search
CPC ... C08J 3/03; C08J 3/005; C08L 17/02; C08L 5/16; C08G 83/007; C08G 2650/04
See application file for complete search history.

(56) References Cited

U.S. PATENT DOCUMENTS

| 2009/0088546 A1* | 4/2009 | Ito ...................... C08B 37/0015 527/300 |
| 2009/0234049 A1 | 9/2009 | Ito et al. |
| 2009/0312490 A1 | 12/2009 | Ito et al. |
| 2013/0296546 A1 | 11/2013 | Yamasaki et al. |
| 2013/0296547 A1 | 11/2013 | Yamasaki et al. |
| 2013/0317209 A1 | 11/2013 | Yamasaki et al. |
| 2013/0331562 A1 | 12/2013 | Yamasaki et al. |

FOREIGN PATENT DOCUMENTS

| CN | 101253212 | 8/2008 | |
| CN | 103102492 | 5/2013 | |
| CN | 103249743 | 8/2013 | |
| CN | 103483506 | 1/2014 | |
| EP | 1 693 399 | 8/2006 | |
| JP | 2007-099978 | 4/2007 | |
| JP | 2010-155880 | 7/2010 | |
| JP | 2010-159336 | 7/2010 | |
| JP | 2010-159337 | 7/2010 | |
| JP | 2010-159337 A * | 7/2010 | ............... C08J 5/18 |
| JP | 2012-188523 | 10/2012 | |
| TW | 201031699 | 9/2010 | |
| TW | 201035186 | 10/2010 | |
| WO | 2005/080469 | 9/2005 | |
| WO | 2012/081431 | 6/2012 | |

* cited by examiner

*Primary Examiner* — Robert D. Harlan
(74) *Attorney, Agent, or Firm* — Hamre, Schumann, Mueller & Larson, P.C.

(57) ABSTRACT

The present invention provides a method for producing an aqueous dispersion of pseudopolyrotaxane that enables the production, by an industrially advantageous method for an aqueous dispersion of pseudopolyrotaxane in which the inclusion amount of a cyclodextrin does not increase with time and which can provide a crosslinked polyrotaxane having sufficient stretchability and breaking strength. The present invention relates to a method for producing an aqueous dispersion of pseudopolyrotaxane containing pseudopolyrotaxane particles in which a polyethylene glycol is included in a cavity of a cyclodextrin molecule in a skewered manner, the method including: an inclusion step of mixing a polyethylene glycol and a cyclodextrin in an aqueous medium to include the polyethylene glycol in a cavity of a cyclodextrin molecule, wherein in the inclusion step, a basic compound is added.

8 Claims, No Drawings

METHOD FOR PRODUCING PSEUDOPOLYROTAXANE AQUEOUS DISPERSION

TECHNICAL FIELD

The present invention relates to methods for producing aqueous dispersions of pseudopolyrotaxane.

BACKGROUND ART

Crosslinked polyrotaxanes are produced by crosslinking polyrotaxanes obtained by introducing capping groups to both ends of a pseudopolyrotaxane. When the pseudopolyrotaxane, for example, is a compound containing a polyethylene glycol (hereinafter also referred to as "PEG") chain (hereinafter also referred to as "PEG compound") and a cyclodextrin that includes the PEG compound, the resulting crosslinked polyrotaxane has a structure in which the cyclodextrin threaded onto the linear molecule of the PEG compound in a skewered manner is movable along the linear chain molecule (pulley effect). External force applied to the crosslinked polyrotaxane thus can be uniformly distributed. The crosslinked polyrotaxanes therefore have excellent characteristics, such as resistance to cracks and flaws, that conventional crosslinked polymers lack.

Pseudopolyrotaxanes used for the production of crosslinked polyrotaxanes are obtained in an aqueous dispersion form as they are typically produced by mixing a polyethylene glycol and a cyclodextrin in an aqueous medium.

Patent Literature 1 discloses a method for producing a polyrotaxane, including: dissolving carboxylated polyethylene glycol (hereinafter also referred to as "PEG-BC") whose PEG chain are carboxylated at both ends and α-cyclodextrin each in 70° C. warm water, mixing the obtained solutions together and cooling the mixture to prepare an aqueous dispersion of pseudopolyrotaxane, freeze-drying the aqueous dispersion to prepare a pseudopolyrotaxane, and reacting the resulting pseudopolyrotaxane with adamantanamine in dimethylformamide in the presence of a BOP reagent (benzotriazole-1-yl-oxy-tris(dimethylamino)phosphonium hexafluorophosphate) as a condensing agent and diisopropylethylamine as a catalyst.

Patent Literature 2 discloses that an aqueous dispersion of pseudopolyrotaxane can be obtained by dissolving a polyethylene glycol and a cyclodextrin into an aqueous medium by heating to 75° C. with stirring, then cooling the mixture to 5° C. with stirring, and continuing stirring at the same temperature for additional 10 hours.

For improved properties of a crosslinked polyrotaxane, it is important that the inclusion amount of the cyclodextrin of the pseudopolyrotaxane is appropriate.

Patent Literature 3, for example, teaches as follows. If the inclusion amount of the cyclodextrin is too small, the resulting crosslinked polyrotaxane has a low crosslinking density, and thus has insufficient dynamic characteristics. If the inclusion amount of the cyclodextrin is too large, that is, if cyclodextrin is too closely packed along the linear molecule, a sliding mode function, in which cyclodextrin molecules relatively move along the linear molecule to maintain a certain distance between them, is not sufficiently exhibited. As a result, the resulting crosslinked polyrotaxane is insufficient in dynamic characteristics such as stretchability or breaking strength.

CITATION LIST

Patent Literature

Patent Literature 1: JP 2007-099978 A
Patent Literature 2: WO 2012/081431
Patent Literature 3: WO 2005/080469

SUMMARY OF INVENTION

Technical Problem

The inclusion amount of a cyclodextrin for a linear molecule has been controlled to an appropriate level by adjustment of the molecular weight of the linear molecule to be included, or adjustment of, for example, the amount to be added, reaction temperature, and dissolved concentration of cyclodextrin in the production of a pseudopolyrotaxane.

In cases where the linear molecule has a small molecular weight, however, in the pseudopolyrotaxane in an aqueous dispersion form, the cyclodextrin inclusion progresses with time, disadvantageously resulting in an aqueous dispersion of pseudopolyrotaxane in which more cyclodextrin than the desired inclusion amount is included.

To solve these problems, the progress of cyclodextrin inclusion has been suppressed by drying the aqueous dispersion of pseudopolyrotaxane within a certain period of time.

In industrial production, however, it is impractical to control the inclusion amount of a cyclodextrin by control of time to dry. There is thus a demand for suppressing the progress of cyclodextrin inclusion in a pseudopolyrotaxane in an aqueous dispersion form.

The present invention has been made in view of such a situation in the art, and aims to provide a method for producing an aqueous dispersion of pseudopolyrotaxane which enables termination of cyclodextrin inclusion in a pseudopolyrotaxane in an aqueous dispersion form and enables maintenance of a desired inclusion amount.

Solution to Problem

The present inventors made intensive studies to solve the above problems. They found out that the inclusion can be terminated by adding a basic compound in an inclusion step in which a polyethylene glycol and a cyclodextrin are mixed in an aqueous medium to include the polyethylene glycol in the cavity of the cyclodextrin molecule. After further studies they completed the present invention.

The present invention relates to the following items.
Item 1.
A method for producing an aqueous dispersion of pseudopolyrotaxane containing pseudopolyrotaxane particles in which a polyethylene glycol is included in a cavity of a cyclodextrin molecule in a skewered manner, the method including: an inclusion step of mixing a polyethylene glycol and a cyclodextrin in an aqueous medium to include the polyethylene glycol in a cavity of a cyclodextrin molecule, wherein in the inclusion step, a basic compound is added.
Item 2.
The method for producing an aqueous dispersion of pseudopolyrotaxane according to Item 1, wherein the basic compound is added in an amount of 0.1 to 10 times the number of moles of reactive groups at both ends of the polyethylene glycol.

Item 3.

The method for producing an aqueous dispersion of pseudopolyrotaxane according to Item 1 or 2, wherein the polyethylene glycol has a mass average molecular weight of 1,000 to 100,000.

Item 4.

The method for producing an aqueous dispersion of pseudopolyrotaxane according to Item 1, 2, or 3, wherein a mass ratio of the polyethylene glycol and the cyclodextrin is 1:2 to 1:5.

Item 5.

A method for producing a polyrotaxane containing a cyclodextrin, a polyethylene glycol included in a cavity of the cyclodextrin in a skewered manner, and capping groups at both ends of the polyethylene glycol, the method including the steps of: producing an aqueous dispersion of pseudopolyrotaxane by the production method according to Item 1, 2, 3, or 4, and introducing capping groups in the aqueous medium constituting the aqueous dispersion of pseudopolyrotaxane after the production step.

Advantageous Effects of Invention

The present invention makes it possible to produce, by an industrially advantageous method, an aqueous dispersion of pseudopolyrotaxane that can suppress an increase with time in the inclusion amount of a cyclodextrin.

DESCRIPTION OF EMBODIMENTS

The method for producing an aqueous dispersion of pseudopolyrotaxane of the present invention is a method for producing an aqueous dispersion of pseudopolyrotaxane containing pseudopolyrotaxane particles in which a polyethylene glycol is included in a cavity of a cyclodextrin molecule in a skewered manner, the method including: an inclusion step of mixing a polyethylene glycol and a cyclodextrin in an aqueous medium to include the polyethylene glycol in a cavity of a cyclodextrin molecule, wherein in the inclusion step, a basic compound is added.

The inclusion step preferably includes a mixing step of dissolving a polyethylene glycol and a cyclodextrin in an aqueous medium to prepare a mixed solution, and a cooling step of cooling the mixed solution to precipitate pseudopolyrotaxane particles.

The polyethylene glycol preferably has a mass average molecular weight of 1,000 to 100,000, more preferably 2,000 to 50,000, still more preferably 4,000 to 35,000. When the mass average molecular weight of the polyethylene glycol is less than 1,000, the resulting crosslinked polyrotaxane may have low mechanical properties. When the mass average molecular weight of the polyethylene glycol is more than 100,000, inclusion itself may be less likely to progress.

The mass average molecular weight as used herein is a polyethylene glycol equivalent value calculated based on the measurement by gel permeation chromatography (GPC). The column used for determination of a polyethylene glycol equivalent mass average molecular weight by GPC is, for example, TSKgel SuperAWM-H (produced by Tosoh Corporation).

The polyethylene glycol preferably has reactive groups at both ends thereof. The reactive groups can be introduced to both ends of the polyethylene glycol by conventionally known methods.

The reactive groups at both ends of the polyethylene glycol are not limited and can be appropriately changed according to the capping groups used. Examples thereof include hydroxy, amino, carboxy, and thiol groups, with a carboxy group being particularly preferred. Examples of the method for introducing carboxy groups to both ends of the polyethylene glycol include a method involving oxidation of both ends of the polyethylene glycol using 2,2,6,6-tetramethyl-1-piperidinyloxy radical (TEMPO) and sodium hypochlorite.

The amount of the carboxy groups introduced to both ends of the PEG can be determined by titration of the carboxy groups of the obtained PEG-BC using a 0.01 mol/L aqueous NaOH solution.

In a preferable embodiment of the present invention, the carboxy groups at both ends of the PEG presumably inhibit cyclodextrin inclusion by forming a carboxylic acid salt with a basic compound such as sodium hydroxide.

In the method for producing an aqueous dispersion of pseudopolyrotaxane of the present invention, the mass ratio between the polyethylene glycol and cyclodextrin mixed in the aqueous medium is preferably 1:2 to 1:5, more preferably 1:2 to 1:4, still more preferably 1:2 to 1:3. A mass of the cyclodextrin of less than twice the mass of the polyethylene glycol may reduce the amount of polyrotaxane to be obtained. A mass of the cyclodextrin of more than five times the mass of the polyethylene glycol does not further increase the inclusion amount, and thus is not economical. In addition, due to the presence of excessive cyclodextrin, the inclusion may progress excessively during the storage of the aqueous dispersion of pseudopolyrotaxane.

Examples of the cyclodextrin include α-cyclodextrin, β-cyclodextrin, γ-cyclodextrin, and derivatives thereof. In particular, α-cyclodextrin is preferred in terms of inclusion properties. These cyclodextrins may be used alone or in combination of two or more thereof.

The aqueous medium may be, for example, water or an aqueous mixture of water and an aqueous organic solvent such as dimethylformamide (DMF) or dimethylsulfoxide (DMSO). Water is particularly preferred.

In the method for producing an aqueous dispersion of pseudopolyrotaxane of the present invention, in mixing the polyethylene glycol and cyclodextrin in the aqueous medium, dissolving the polyethylene glycol and cyclodextrin by heating to usually 50° C. to 100° C., preferably 60° C. to 90° C., more preferably 70° C. to 80° C. can provide a substantially transparent mixed solution.

When the method for producing an aqueous dispersion of pseudopolyrotaxane of the present invention includes the cooling step, the cooling step is preferably performed by continuously or intermittently cooling the mixed solution while flowing the mixed solution. Precipitating pseudopolyrotaxane particles by continuously or intermittently cooling the mixed solution while flowing the mixed solution can provide an aqueous dispersion of pseudopolyrotaxane with good fluidity that does not decrease with time.

The temperature reached in the cooling step is preferably 0° C. to 30° C., more preferably 5° C. to 20° C., still more preferably 5° C. to 15° C. Cooling the mixed solution to lower than 0° C. may cause freezing or the like to decrease the fluidity of the aqueous dispersion of pseudopolyrotaxane. When the temperature reached is higher than 30° C., pseudopolyrotaxane particles may not sufficiently precipitate.

In the cooling step, the mixed solution is cooled at a cooling rate of preferably 0.01 to 30° C./min, more preferably 0.05 to 20° C./min, still more preferably 0.05 to 10° C./min. A cooling rate of lower than 0.01° C./min causes precipitation of too fine pseudopolyrotaxane particles, resulting in low fluidity of the aqueous dispersion of pseudopolyrotaxane. A cooling rate of higher than 30° C./min leads to large pseudopolyrotaxane particles and thus to low dispersion stability, which may cause sedimentation.

For more thorough precipitation of pseudopolyrotaxane particles, the mixed solution can be intermittently cooled, as described above. Also, the cooling rate and the flowing state of the mixed solution can be changed during the cooling process.

When the cooling step is performed while flowing the mixed solution, the mixed solution may be flowed by stirring with a stirring blade, ultrasonic irradiation, or other methods.

The degree of flowing of the mixed solution is not limited, and may be optionally selected from the range of slight flowing of the mixed solution by gentle stirring to vigorous flowing by vigorous stirring using a homogenizer and the like. Excessively weak flowing may precipitate large pseudopolyrotaxane particles, which may decrease the dispersion stability and cause sedimentation. Excessively vigorous flowing may precipitate too fine pseudopolyrotaxane particles, leading to low fluidity of the resulting aqueous dispersion of pseudopolyrotaxane.

In the method for producing an aqueous dispersion of pseudopolyrotaxane of the present invention, a basic compound is added in the inclusion step.

This suppresses an increase in the inclusion amount of the cyclodextrin with time in the aqueous dispersion of pseudopolyrotaxane. This phenomenon is presumably resulted from the termination of inclusion.

Examples of the basic compound include hydroxides such as sodium hydroxide, potassium hydroxide, calcium hydroxide, and cesium hydroxide, primary amines such as methylamine, secondary amines such as dimethylamine, tertiary amines such as triethylamine and N,N-diisopropylethylamine, and cyclic amines such as pyridine, morpholine, and diazabicycloundecene. These basic compounds may be used alone or in combination of two or more thereof.

The amount by mass of the basic compound added is preferably 0.0062 to 305 parts by mass, more preferably 0.018 to 61 parts by mass, still more preferably 0.031 to 55 parts by mass, particularly preferably 0.037 to 50 parts by mass, relative to 100 parts by mass of the polyethylene glycol. The amount by mole of the basic compound added is preferably 0.2 to 20 times, more preferably 0.6 to 4 times, still more preferably 1.0 to 3.6 times, particularly preferably 1.2 to 3.2 times the number of moles of the polyethylene glycol. An amount of the basic compound added of less than 0.0062 parts by mass (or less than 0.2 times the number of moles of the polyethylene glycol) may reduce the cyclodextrin inclusion terminating effect. An amount of the basic compound added of more than 305 parts by mass (or more than 20 times the number of moles of the polyethylene glycol) does not further increase the cyclodextrin inclusion terminating effect, and thus is not economical.

The amount of the basic compound added is preferably 0.1 to 10 times, more preferably 0.3 to 2 times, still more preferably 0.5 to 1.8 times, particularly preferably 0.6 to 1.6 times the number of moles of the reactive groups at both ends of the polyethylene glycol. An amount of the basic compound added of less than 0.1 times the number of moles of the capping groups may reduce the cyclodextrin inclusion terminating effect. An amount of the basic compound added of more than 10 times the number of moles of the capping groups does not further increase the cyclodextrin inclusion terminating effect, and thus is not economical.

The basic compound may be added in one portion or in multiple portions. In particular, the basic compound is preferably added in one portion in order to allow the reactive groups at both ends of the PEG and the basic compound to react at a time.

The "amount of the basic compound added" as used herein refers to the total amount of the basic compound added in the inclusion step. That is, when the basic compound is added in multiple separate portions, the term refers to the overall amount of the basic compound added.

The temperature at which the basic compound is added is preferably 0° C. to 60° C., more preferably 5° C. to 40° C. When the temperature at which the basic compound is added is lower than 0° C., the aqueous dispersion of pseudopolyrotaxane may have a decreased fluidity due to freezing or the like. When the temperature is higher than 60° C., the inclusion reaction may progress insufficiently, leading to a decrease in the inclusion rate or a decrease in the amount of the pseudopolyrotaxane to be obtained.

After the addition of the basic compound, the obtained solution containing the basic compound is preferably stirred.

The stirring time after the addition of the basic compound is preferably 1 to 60 minutes. A stirring time of less than 1 minute causes the basic compound to be in a non-uniform state in the aqueous dispersion of pseudopolyrotaxane, which may lead to an insufficient inclusion terminating effect. A stirring time of longer than 60 minutes does not further enhance the inclusion terminating effect and thus is not economical.

The basic compound may be added by a method such as direct addition of the basic compound or the addition of a solution of the basic compound. In particular, the addition of a solution of the basic compound is preferred. In the case of employing the addition of a solution of the basic compound, the solvent for dissolving the basic compound is preferably water.

In the case of employing the addition of a solution of the basic compound, the solution may contain the basic compound at any concentration. The concentration can be appropriately adjusted according to the type of the basic compound to be added. Preferably the concentration is 0.1 to 60% by mass, more preferably 1 to 40% by mass. When the concentration of the basic compound is less than 0.1% by mass, an increased amount of the basic compound solution is added, leading to a lower solids content and thus to an increase in the amount of water to be removed in the subsequent drying step. Such a concentration is thus not economical. When the concentration of the basic compound is more than 60% by mass, the basic compound may be insufficiently dissolved.

When the inclusion step includes the mixing step and the cooling step, the basic compound may be added to the mixed solution prepared in the mixing step, may be added to the mixed solution during cooling in the cooling step, or may be added to the aqueous dispersion of pseudopolyrotaxane in which pseudopolyrotaxane particles has been precipitated by the cooling step. In order to maintain good fluidity of the aqueous dispersion of pseudopolyrotaxane, the basic compound is preferably added after the completion of the cooling step.

The concentration of the pseudopolyrotaxane (hereinafter also "solids concentration") in the aqueous dispersion of pseudopolyrotaxane is preferably 5 to 25% by mass, more preferably 5 to 20% by mass, still more preferably 10 to 20% by mass. A solids concentration of the aqueous dispersion of pseudopolyrotaxane of less than 5% by mass is not economical. A solids concentration of the aqueous dispersion of pseudopolyrotaxane of more than 25% by mass may reduce the fluidity of the aqueous dispersion of pseudopolyrotaxane.

Introducing capping groups to both ends of the polyethylene glycol of the pseudopolyrotaxane in the aqueous dispersion of pseudopolyrotaxane provides a polyrotaxane capped to prevent the release of the cyclodextrin from the polyethylene glycol chain (a polyrotaxane including a cyclodextrin, a polyethylene glycol included in the cavity of the cyclodextrin in a skewered manner, and capping groups at the both ends of the polyethylene glycol). The capping groups can be introduced to the both ends of the polyethylene glycol of the pseudopolyrotaxane by a conventionally known method (e.g., the method disclosed in JP 2005-154675 A).

More specifically, for example, the introduction of capping groups to both ends of the polyethylene glycol in the pseudopolyrotaxane can be conducted in a medium that dissolves the pseudopolyrotaxane (e.g., dimethylformamide) or in a medium that does not dissolve the pseudopolyrotaxane, after drying the aqueous dispersion of pseudopolyrotaxane. Alternatively, for example, the introduction of capping groups can be conducted in the aqueous medium constituting the aqueous dispersion of pseudopolyrotaxane. The introduction of capping groups in the aqueous medium can be conducted by a method such as that disclosed in WO 2014/045921.

Particularly preferred is the introduction of capping groups in the aqueous medium constituting the aqueous dispersion of pseudopolyrotaxane because it eliminates the need for the step of drying the aqueous dispersion of pseudopolyrotaxane.

Examples of the aqueous medium include aqueous organic solvents such as dimethylformamide, dimethylacetamide, dimethylsulfoxide, acetone, methyl ethyl ketone, methanol, ethanol, isopropanol, ethylene glycol, propylene glycol, glycerin, and tetrahydrofuran, mixed solvents of water and any of these aqueous organic solvents, and water.

Examples of the capping groups include dinitrophenyl group, adamantane group, anthracene group, trityl group, cyclodextrins, fluoresceins, pyrenes, and derivatives thereof.

The present invention is described below in more detail based on examples which, however, are not intended to limit the scope of the present invention. In the following, PEG having carboxyl groups at both ends of the PEG chain was produced by oxidizing a polyethylene glycol (PEG) with reference to the method described in WO 2006/115255.

Production Example 1

In a 500-mL flask, 48 g of PEG (mass average molecular weight 11,000), 0.048 g of 2,2,6,6-tetramethyl-1-piperidinyloxy radical (TEMPO), and 4.5 g of sodium bromide were dissolved in 138 mL of water. To the solution was then added 30 mL of an aqueous sodium hypochlorite solution (available chlorine concentration 5%), followed by stirring at room temperature for 30 minutes. An amount of 30 mL of ethanol was added to decompose the excess of sodium hypochlorite, whereby the reaction was terminated.

The organic layer was isolated with a separatory funnel by repeating extraction using 80 mL of methylene chloride three times. The methylene chloride was then distilled off using an evaporator. The resulting substance was dissolved in 400 mL of warm ethanol before allowed to stand in a freezer (−4° C.) overnight, whereby 48 g of PEG having carboxy groups at both ends was obtained. Titration using 0.01 mol/L NaOH showed that the end carboxy groups introduced to the PEG was 0.00024 mol/g.

Example 1

A 2-L flask equipped with a stirrer was charged with 840 mL of water, 48 g of the PEG prepared in Preparation Example 1 having carboxy groups at both ends, and 144 g of α-cyclodextrin. The mixture was heated to 80° C. with stirring using the stirring blade to dissolve the PEG and α-cyclodextrin in the aqueous medium. Thus a mixed solution was obtained. The mixed solution was then cooled at a cooling rate of 0.4° C./min to 5° C., and further stirring was continued for one hour at the same temperature, whereby an emulsion-like aqueous dispersion of pseudopolyrotaxane with good fluidity was obtained. To this aqueous dispersion of pseudopolyrotaxane was added 1.5 mL (NaOH 10.0 mol/L) of a 30% by mass aqueous NaOH solution, followed by stirring for 15 minutes, whereby 1033 g of an aqueous dispersion of pseudopolyrotaxane (solids concentration 18.6% by mass) was obtained.

Example 2

A 2-L flask equipped with a stirrer was charged with 735 mL of water, 48 g of the PEG prepared in Preparation Example 1 having carboxy groups at both ends, and 120 g of α-cyclodextrin. The mixture was heated to 80° C. with stirring using the stirring blade to dissolve the PEG and α-cyclodextrin in the aqueous medium. Thus a mixed solution was obtained. The mixed solution was then cooled at a cooling rate of 0.4° C./min to 5° C., and further stirring was continued for one hour at the same temperature, whereby an emulsion-like aqueous dispersion of pseudopolyrotaxane with good fluidity was obtained. To this aqueous dispersion of pseudopolyrotaxane was added 1.5 mL (NaOH 10.0 mol/L) of a 30% by mass aqueous NaOH solution, followed by stirring for 15 minutes, whereby 904 g of an aqueous dispersion of pseudopolyrotaxane (solids concentration 18.6% by mass) was obtained.

Example 3

A 2-L flask equipped with a stirrer was charged with 628 mL of water, 48 g of the PEG prepared in Preparation Example 1 having carboxy groups at both ends, and 96 g of α-cyclodextrin. The mixture was heated to 80° C. with stirring using the stirring blade to dissolve the PEG and α-cyclodextrin in the aqueous medium. Thus a mixed solution was obtained. The mixed solution was then cooled at a cooling rate of 0.4° C./min to 5° C., and further stirring was continued for one hour at the same temperature, whereby an emulsion-like aqueous dispersion of pseudopolyrotaxane with good fluidity was obtained. To this aqueous dispersion of pseudopolyrotaxane was added 1.5 mL (NaOH 10.0 mol/L) of a 30% by mass aqueous NaOH solution, followed by stirring for 15 minutes, whereby 772 g of an aqueous dispersion of pseudopolyrotaxane (solids concentration 18.6% by mass) was obtained.

Example 4

A 2-L flask equipped with a stirrer was charged with 840 mL of water, 48 g of the PEG prepared in Preparation Example 1 having carboxy groups at both ends, and 144 g of α-cyclodextrin. The mixture was heated to 80° C. with stirring using the stirring blade to dissolve the PEG and α-cyclodextrin in the aqueous medium. Thus a mixed solution was obtained. The mixed solution was then cooled at a cooling rate of 0.4° C./min to 5° C., and further stirring was continued for one hour at the same temperature, whereby an emulsion-like aqueous dispersion of pseudopolyrotaxane with good fluidity was obtained. To this aqueous dispersion of pseudopolyrotaxane was added 1.8 mL (NaOH 10.0 mol/L) of a 30% by mass aqueous NaOH solution, followed by stirring for 15 minutes, whereby 1033 g of an aqueous dispersion of pseudopolyrotaxane (solids concentration 18.6% by mass) was obtained.

Example 5

A 2-L flask equipped with a stirrer was charged with 840 mL of water, 48 g of the PEG prepared in Preparation Example 1 having carboxy groups at both ends, and 144 g of α-cyclodextrin. The mixture was heated to 80° C. with stirring using the stirring blade to dissolve the PEG and α-cyclodextrin in the aqueous medium. Thus a mixed solution was obtained. The mixed solution was then cooled at a cooling rate of 0.4° C./min to 5° C., and further stirring was continued for one hour at the same temperature, whereby an emulsion-like aqueous dispersion of pseudopolyrotaxane with good fluidity was obtained. To this aqueous dispersion of pseudopolyrotaxane was added 16.0 mL (KOH 0.89 mol/L) of a 5% by mass aqueous KOH solution, followed by stirring for 15 minutes, whereby 1048 g of an aqueous dispersion of pseudopolyrotaxane (solids concentration 18.3% by mass) was obtained.

Example 6

A 2-L flask equipped with a stirrer was charged with 840 mL of water, 48 g of the PEG prepared in Preparation Example 1 having carboxy groups at both ends, and 144 g of α-cyclodextrin. The mixture was heated to 80° C. with stirring using the stirring blade to dissolve the PEG and α-cyclodextrin in the aqueous medium. Thus a mixed solution was obtained. The mixed solution was then cooled at a cooling rate of 0.4° C./min to 5° C., and further stirring was continued for one hour at the same temperature, whereby an emulsion-like aqueous dispersion of pseudopolyrotaxane with good fluidity was obtained. To this aqueous dispersion of pseudopolyrotaxane was added a 10.5 mL (Ca(OH)$_2$ 0.67 mol/L) of 5% by mass aqueous Ca(OH)$_2$ solution, followed by stirring for 15 minutes, whereby 1042 g of an aqueous dispersion of pseudopolyrotaxane (solids concentration 18.4% by mass) was obtained.

Example 7

A 2-L flask equipped with a stirrer was charged with 840 mL of water, 48 g of the PEG prepared in Preparation Example 1 having carboxy groups at both ends, and 144 g of α-cyclodextrin. The mixture was heated to 80° C. with stirring using the stirring blade to dissolve the PEG and α-cyclodextrin in the aqueous medium. Thus a mixed solution was obtained. The mixed solution was then cooled at a cooling rate of 0.4° C./min to 5° C., and further stirring was continued for one hour at the same temperature, whereby an emulsion-like aqueous dispersion of pseudopolyrotaxane with good fluidity was obtained. To this aqueous dispersion of pseudopolyrotaxane was added 2.7 mL (DIEA 5.6 mol/L) of a 98% by mass N,N-diisopropylethylamine (DIEA) solution, followed by stirring for 15 minutes, whereby 1033 g of an aqueous dispersion of pseudopolyrotaxane (solids concentration 18.6% by mass) was obtained.

Example 8

A 2-L flask equipped with a stirrer was charged with 840 mL of water, 48 g of the PEG prepared in Preparation Example 1 having carboxy groups at both ends, and 144 g of α-cyclodextrin. The mixture was heated to 80° C. with stirring using the stirring blade to dissolve the PEG and α-cyclodextrin in the aqueous medium. Thus a mixed solution was obtained. The mixed solution was then cooled at a cooling rate of 0.4° C./min to 5° C., and further stirring was continued for one hour at the same temperature, whereby an emulsion-like aqueous dispersion of pseudopolyrotaxane with good fluidity was obtained. To this aqueous dispersion of pseudopolyrotaxane was added 2.3 mL (DBU 6.5 mol/L) of a 97% by mass diazabicycloundecene (DBU) solution, followed by stirring for 15 minutes, whereby 1034 g of an aqueous dispersion of pseudopolyrotaxane (solids concentration 18.6% by mass) was obtained.

Comparative Example 1

An aqueous dispersion of pseudopolyrotaxane was obtained in the same manner as in Example 1 except that 1.5 mL of a 30% by mass aqueous NaOH solution was not added.

Comparative Example 2

An aqueous dispersion of pseudopolyrotaxane was obtained in the same manner as in Example 2 except that 1.5 mL of a 30% by mass aqueous NaOH solution was not added.

Comparative Example 3

An aqueous dispersion of pseudopolyrotaxane was obtained in the same manner as in Example 3 except that 1.5 mL of a 30% by mass aqueous NaOH solution was not added.

(Evaluation)
(Inclusion Rate Measurement)

The inclusion rate of the aqueous dispersion of pseudopolyrotaxanes obtained in Examples 1 to 8 and Comparative Examples 1 to 3 was measured by the following method. Table 1 shows the results.

(1) Drying of Aqueous Dispersion of Pseudopolyrotaxane

To each of the aqueous dispersion of pseudopolyrotaxanes obtained in Examples 1 to 8 and Comparative Examples 1 to 3 was added hydrochloric acid in an equimolar amount to the basic compound added to the dispersion (in Example 6, twice the amount (by mole) of the basic compound). The mixture was freeze-dried to prepare a pseudopolyrotaxane.

Separately, the aqueous dispersion of pseudopolyrotaxanes obtained in Examples 1 to 8 and Comparative Examples 1 to 3 were each stored in a refrigerator (5° C. to 10° C.) for a predetermined period of time (48 hours and 480 hours in Examples 1 and 4 to 8 and Comparative Example 1; 48 hours and 600 hours in Examples 2 and 3 and Comparative Examples 2 and 3). After storage, hydrochloric acid was added in an equimolar amount to the basic compound added to the dispersion (in Example 6, twice the amount (by mole) of the basic compound). Thereafter, the resulting mixtures were freeze-dried to prepare pseudopolyrotaxanes that were different in storage time for the aqueous dispersion of pseudopolyrotaxane.

(2-1) Capping of Pseudopolyrotaxane

At room temperature, 3.4 g of adamantanamine hydrochloride was dissolved into 180 mL of dimethylformamide (DMF). To the solution was added 64 g of the pseudopolyrotaxane powder obtained in "(1) Drying of aqueous dispersion of pseudopolyrotaxane", immediately followed by thorough shaking. Subsequently, the mixture was added to a solution of 2.9 g of BOP reagent (benzotriazole-1-yl-oxy-tris(dimethylamino)phosphonium hexafluorophosphate) in 30 mL of DMF, followed by through shaking to prepare a mixture. The obtained mixture was allowed to react at 60° C. for one hour. The mixture was then filtered to obtain wet cake of a polyrotaxane in which the polyethylene glycol of the pseudopolyrotaxane was capped at both ends with adamantanamine. This wet cake was washed with 80° C. warm water four times, whereby purified polyrotaxane was obtained.

(2-2) Capping of Pseudopolyrotaxane

To 344 g of each of the aqueous dispersion of pseudopolyrotaxanes obtained in Example 1 and Comparative Example 1 were added first hydrochloric acid in an equimolar amount to the basic compound added, and next 3.3 g of adamantanamine hydrochloride as a capping agent, 3.1 g of 2-chloro-4,6-dimethoxy-1,3,5-triazine, and 2.2 g of N-methylmorpholine, with stirring using a stirring blade at 700 rpm. The temperature was raised to and held at 60° C. for four hours. The obtained mixture was then centrifuged and the supernatant was removed, whereby wet cake of a polyrotaxane was obtained in which the polyethylene glycol of the pseudopolyrotaxane was capped at both ends with adamantanamine. This wet cake was mixed with 192 g of water, warmed to 70° C. with stirring, and stirred at this temperature for 60 minutes. Centrifugation was performed again and the supernatant was removed. This washing procedure was repeated two additional times, whereby purified polyrotaxane was obtained.

(2-3) Capping of Pseudopolyrotaxane

To 344 g of each of the aqueous dispersion of pseudopolyrotaxanes obtained in Example 1 and Comparative Example 1 were added first 111 g of sodium chloride, next hydrochloric acid in an equimolar amount to the basic compound added, and then 3.3 g of adamantanamine hydrochloride as a capping agent, 3.1 g of 2-chloro-4,6-dimethoxy-1,3,5-triazine, and 2.2 g of N-methylmorpholine, with stirring using a stirring blade at 700 rpm. The temperature was raised to and held at 60° C. for four hours. The obtained mixture was then centrifuged and the supernatant was removed, whereby wet cake of a polyrotaxane was obtained in which the polyethylene glycol of the pseudopolyrotaxane was capped at both ends with adamantanamine. This wet cake was mixed with 192 g of water, warmed to 70° C. with stirring, and stirred at this temperature for 60 minutes. Centrifugation was performed again and the supernatant was removed. This washing procedure was repeated two additional times, whereby purified polyrotaxane was obtained.

(3) Inclusion Rate Measurement

The inclusion rate of each obtained purified polyrotaxane was identified by $^1$H-NMR. The obtained inclusion rate can be regarded as the inclusion rate of the pseudopolyrotaxane.

The "inclusion rate" as used herein means the ratio of cyclodextrin including the PEG to the maximum inclusion amount of the cyclodextrin for the PEG. Specifically, The inclusion rate is calculated by dissolving the obtained purified polyrotaxane in DMSO-$d_6$, subjecting the solution to measurement with a NMR measuring device (VARIAN Mercury-400BB produced by Varian Technologies Japan Ltd.), and comparing the integrated value of a cyclodextrin peak at 4 to 6 ppm and the integrated value of a cyclodextrin peak and a PEG peak at 3 to 4 ppm.

TABLE 1

| | PEG having carboxy groups at both ends | | | Basic compound | | | The number of moles of basic compound/ The number of moles of carboxy groups at both ends of PEG | Capping Step | | Evaluation α-cyclodextrin inclusion rate after storage of aqueous dispersion of pseudopolyrotaxane for a predetermined period of time Storage time | | |
|---|---|---|---|---|---|---|---|---|---|---|---|---|
| | Charge (g) | The number of moles of carboxy groups at both ends of PEG (mol) | Charge of α-cyclodextrin (g) | Type | Concentration of aqueous solution (% by mass) | Charge (mL) | The number of moles (mol) | Procedure | Solvent | 0 hour | 48 hours | 480 hours (600 hours) |
| Example 1 | 48 | 0.01152 | 144 | NaOH | 30 | 1.5 | 0.015 | 1.30 | (2-1) | DMF | 0.31 | 0.30 | 0.29 |
| | | | | | | | | | (2-2) | Water | 0.31 | 0.31 | 0.32 |
| | | | | | | | | | (2-3) | Water | 0.30 | 0.30 | 0.31 |
| Example 2 | 48 | 0.01152 | 120 | NaOH | 30 | 1.5 | 0.015 | 1.30 | (2-1) | DMF | 0.24 | 0.24 | 0.23 |
| Example 3 | 48 | 0.01152 | 96 | NaOH | 30 | 1.5 | 0.015 | 1.30 | (2-1) | DMF | 0.24 | 0.23 | 0.23 |
| Example 4 | 48 | 0.01152 | 144 | NaOH | 30 | 1.8 | 0.018 | 1.57 | (2-1) | DMF | 0.31 | 0.31 | 0.30 |
| Example 5 | 48 | 0.01152 | 144 | KOH | 5 | 16.0 | 0.014 | 1.22 | (2-1) | DMF | 0.30 | 0.30 | 0.31 |
| Example 6 | 48 | 0.01152 | 144 | Ca(OH)$_2$ | 5 | 10.5 | 0.007 | 0.61 | (2-1) | DMF | 0.30 | 0.31 | 0.30 |
| Example 7 | 48 | 0.01152 | 144 | DIEA | 98 | 2.7 | 0.015 | 1.30 | (2-1) | DMF | 0.31 | 0.30 | 0.29 |
| Example 8 | 48 | 0.01152 | 144 | DBU | 97 | 2.3 | 0.015 | 1.30 | (2-1) | DMF | 0.29 | 0.30 | 0.29 |
| Comparative Example 1 | 48 | 0.01152 | 144 | — | 0 | 0 | 0 | 0 | (2-1) | DMF | 0.31 | 0.33 | 0.37 |
| | | | | | | | | | (2-2) | Water | 0.31 | 0.34 | 0.38 |
| | | | | | | | | | (2-3) | Water | 0.32 | 0.33 | 0.37 |
| Comparative Example 2 | 48 | 0.01152 | 120 | — | 0 | 0 | 0 | 0 | (2-1) | DMF | 0.24 | 0.29 | 0.37 |
| Comparative Example 3 | 48 | 0.01152 | 96 | — | 0 | 0 | 0 | 0 | (2-1) | DMF | 0.24 | 0.26 | 0.30 |

INDUSTRIAL APPLICABILITY

The present invention provides a method for producing an aqueous dispersion of pseudopolyrotaxane that enables the production, in an industrially advantageous manner, of an aqueous dispersion of pseudopolyrotaxane in which the inclusion amount of a cyclodextrin does not increase with time and which can provide crosslinked polyrotaxane having sufficient stretchability and breaking strength.

The invention claimed is:

1. A method for producing an aqueous dispersion of a pseudopolyrotaxane containing pseudopolyrotaxane particles in which a polyethylene glycol is included in a cavity of a cyclodextrin molecule in a skewered manner, the method comprising:
an inclusion step of mixing the polyethylene glycol and a molecular cyclodextrin in an aqueous medium to include the polyethylene glycol in the cavity of the cyclodextrin molecule,
wherein the inclusion step includes a mixing step of dissolving the polyethylene glycol and the cyclodextrin in the aqueous medium to prepare a mixed solution, and a cooling step of cooling the mixed solution to precipitate pseudopolyrotaxane particles, and
a basic compound is added after the pseudopolyrotaxane has been precipitated in the cooling step.

2. The method for producing the aqueous dispersion of the pseudopolyrotaxane according to claim 1,
wherein the basic compound is added in an amount of 0.1 to 10 times the number of moles of reactive groups at both ends of the polyethylene glycol.

3. The method for producing the aqueous dispersion of the pseudopolyrotaxane according to claim 1,
wherein the polyethylene glycol has a mass average molecular weight of 1,000 to 100,000.

4. The method for producing the aqueous dispersion of the pseudopolyrotaxane according to claim 1,
wherein a mass ratio of the polyethylene glycol and the cyclodextrin is 1:2 to 1:5.

5. A method for producing a polyrotaxane containing a cyclodextrin, a polyethylene glycol included in a cavity of the cyclodextrin in a skewered manner, and capping groups at both ends of the polyethylene glycol,
the method comprising the steps of:
producing an aqueous dispersion of a pseudopolyrotaxane by the production method according to claim 1, and
introducing capping groups in an aqueous medium constituting the aqueous dispersion of the pseudopolyrotaxane after the production step.

6. The method for producing the aqueous dispersion of the pseudopolyrotaxane according to claim 1,
wherein a temperature in mixing the polyethylene glycol and the cyclodextrin in the aqueous medium is from 50° C. to 100° C.

7. The method according to claim 1, wherein the molecular cyclodextrin is α-cyclodextrin, β-cyclodextrin, or γ-cyclodextrin.

8. The method according to claim 1, wherein the basic compound suppresses an increase in an inclusion amount of the cyclodextrin with time in the aqueous dispersion of the pseudopolyrotaxane.

* * * * *